United States Patent
Triantafyllou

(12) 
(10) Patent No.: US 6,451,369 B1
(45) Date of Patent: *Sep. 17, 2002

(54) NON-DAIRY, READY-TO-USE MILK SUBSTITUTE, AND PRODUCTS MADE THEREWITH

(75) Inventor: Angeliki Öste Triantafyllou, Lund (SE)

(73) Assignee: Cereal Base CEBA AB, Lund (SE)

( * ) Notice: Subject to any disclaimer, the term of this patent is extended or adjusted under 35 U.S.C. 154(b) by 7 days.

This patent is subject to a terminal disclaimer.

(21) Appl. No.: 09/784,685

(22) Filed: Feb. 15, 2001

Related U.S. Application Data

(63) Continuation-in-part of application No. 09/302,127, filed on Apr. 29, 1999, now Pat. No. 6,190,708.
(60) Provisional application No. 60/106,224, filed on Oct. 30, 1998, and provisional application No. 60/104,706, filed on Oct. 19, 1998.

(51) Int. Cl.$^7$ ............................................... A23L 1/105
(52) U.S. Cl. ...................................................... 426/618
(58) Field of Search ............................. 426/44, 18, 20, 426/21, 28, 52, 618, 629, 456, 459, 460, 462, 463, 590, 598, 565

(56) References Cited

U.S. PATENT DOCUMENTS

| | | | |
|---|---|---|---|
| 4,834,988 A | * 5/1989 | Karwowski et al. | ........... 426/20 |
| 4,996,063 A | * 2/1991 | Inglett | ........................ 426/21 |
| 5,686,123 A | * 11/1997 | Lindahl et al. | ............... 426/28 |

FOREIGN PATENT DOCUMENTS

| | | | |
|---|---|---|---|
| EP | 83106388 | * | 1/1984 |
| EP | 86850418 | * | 8/1987 |
| EP | 93304705 | * | 1/1994 |
| GB | 1495220 | * | 12/1977 |
| WO | 95/27407 | * | 10/1995 |

OTHER PUBLICATIONS

Kessler, H.G., Kessler, Verlay A. Food Engineering and Dairy Technology, 1981, Chapter 6, pp. 139–207.*

* cited by examiner

*Primary Examiner*—Keith Hendricks
(74) *Attorney, Agent, or Firm*—Simpson & Simpson, PLLC

(57) ABSTRACT

Efficient, selective, and economical methods for producing non-dairy ready-to-use milk substitute cereal dispersions having intact β-glucans, proteins, and natural sugars, while retaining the aroma and flavor of natural cereal. The methods include treating a cereal substrate suspension with an enzyme preparation that comprises at least one hydrolase having the ability to hydrolyze α-glycosidic bonds and having no glucanase and proteinase effect. The hydrolase may be selected from the group consisting of β-amylase, α-amylase, amyloglucosidase and pullulanase, with the proviso that when the enzyme preparation comprises α-amylase or β-amylase, there is always a mixture of at least one other of the α-glycosidic hydrolases. When β-amylase and α-amylase are selected, they are used as a mixture, i.e., introduced simultaneously, to provide for accelerated enzymatic hydrolysis and for reduced amounts of the enzymes than otherwise needed if the enzymes were used separately. In addition to the above-identified hydrolases, the enzyme preparations of the present invention may further comprise an isomerase, such as glucose isomerase.

14 Claims, No Drawings

NON-DAIRY, READY-TO-USE MILK SUBSTITUTE, AND PRODUCTS MADE THEREWITH

CROSS-REFERENCES

This application is a Continuation-in-part of U.S. application Ser. No. 09/302,127 filed Apr. 29, 1999, now U.S. Pat. No. 6,190,708 which claims the benefit of U.S. Provisional Application No. 60/106,224, filed Oct. 30, 1998 and U.S. Provisional Application No. 60/104,706, filed Oct. 19, 1998.

FIELD OF THE INVENTION

The present invention relates generally to non-dairy cereal dispersions prepared by enzymatic hydrolysis and more specifically, to non-dairy oat dispersions prepared by synergistic enzymatic hydrolysis and to the products produced therefrom, such as non-dairy, ready-to-use milk substitutes, yogurt, ice cream, and the like.

BACKGROUND

The beneficial health effects of dietary fibers are well known. In this context, there has been a growing interest in food products made from cereal grains, such as oats and barley. In many respects, however, oats offer more health benefits than do other cereals.

Oats have a higher protein and fat content than do other cereals and, in addition, the proteins in oats are of higher food value than are those found in other cereals. Oat grains also have a higher concentration of beta-glucans, which are believed to lower the serum cholesterol level of hypercholesteremic individuals, and as a raised serum cholesterol concentration is associated with an increased risk of heart disease, it is important to be able to include foods high in beta-glucans in one's daily diet (as disclosed in Consumption of Oat Milk for 5 Weeks Lowers Serum Cholesterol and LDL Cholesterol in Free-Living Men with Moderate Hypercholesterolemia, 1999, *Nutrition & Metabolism* 43:301–309, the contents of which are incorporated by reference herein). Additionally, oats have a high content of soluble fiber (most of which is beta-glucans), and foods containing soluble dietary fiber have also been shown to decrease serum cholesterol concentration. Oats also have a lower carbohydrate content than comparable cereals, contain considerable proportions of mono and polyunsaturated fats, and many essential amino acids, and minerals.

In oats, the most nutritious components are distributed fairly evenly in the whole grain, whereas in other grains, the nutritious components are frequently concentrated in specific parts of the grain. This means that when using oats, once the hull has been removed, the whole grain can be used for making various products.

The nutritional aspects of oat components have prompted the introduction of oats, or parts thereof, into several different food products. For instance, U.S. Pat. No. 4,996,063 (G. F. Inglett) discloses the preparation of water-soluble dietary fiber compositions by treating ground oat products with α-amylases. The α-amylase serves to thin the oat starch, and any α-amylase may thus be used. The produced pulverulent dietary fiber compositions are used as additives in food products, such as fat substitutes. However, these products not only lack desirable aromatics of natural oats, but are also deprived of agreeable natural oat flavorings.

U.S. Pat. No. 5,686,123 (to L. Lindahl et al.) discloses a homogeneous and stable cereal suspension having the taste and aroma of natural oats. The disclosed cereal suspension is prepared by treating a suspension of oatmeal with beta-amylase, which has no glucanase and proteinase activity, in a first enzyme treatment step, which specifically generates maltose and maltodextrin units. Then in a second enzyme treatment step, the suspension is treated with α-amylase, which also has no glucanase and proteinase activity, and which specifically generates maltose units. This oat suspension is a milky product, which can be used as an alternative to milk, especially for lactose-intolerant people. It may also be used as the basis of or an additive in the manufacture of ice cream, gruel, yogurt, milkshakes, health beverages, and snacks. However, this process is time consuming because of the sequential treatments with different hydrolases, thereby increasing the cost of production. Moreover, sequential enzyme treatments eliminate any possible positive synergic effects that may occur when enzymes are used simultaneously. Furthermore, the overall viscosity and/or sugar content of the cereal suspension cannot be efficiently controlled or manipulated.

In view of these shortcomings, there is a need for cereal dispersions, including ready-to-use, non-dairy whole milk substitutes and products containing such milk substitutes, which can be made using enzyme preparations which hydrolyze cereal starch in a more cost-efficient and timely manner while producing a nutritious, lactose free cereal dispersion which retains the flavor and aromatic qualities of the natural cereal, and in which the viscosity, sugar content, and overall texture can be regulated or modified for a preferred end product, while maintaining cholesterol lowering properties.

SUMMARY

Accordingly, the present invention is directed to non-dairy cereal dispersions that satisfy these needs.

Thus, it is a principal object of the present invention to provide for non-dairy cereal dispersions made using enzyme preparations, which hydrolyze cereal starch in a cost-efficient and timely manner.

It is another object to produce nutritious, non-dairy, lactose free cereal dispersions, which retain the flavor and aromatic qualities of the natural cereal.

It is yet another object to produce cereal dispersions in which the viscosity, sugar content, and overall texture can be regulated or manipulated by varying the relative amounts of the enzymes used, while maintaining a high concentration of natural sugars, proteins, and of beta-glucans which provide cholesterol lowering properties.

A still further objective is to provide ready-to-use and consume, non-dairy milk substitute oat milks each having a sugar and maltodextrin composition, and a viscosity value that can be related to the enzyme preparation used, wherein the oat milks can be used directly for drinking and for cooking in place of dairy milk, or that can be further treated to provide for a range of products, including concentrates and powdered products, and ready-to-consume products, such as ice cream and yogurt.

These objectives are met by non-dairy cereal dispersions comprising a cereal substrate suspension and an enzyme composition for the enzymatic hydrolysis of the constituents in the cereal substrate suspension, wherein the heat-treated, enzyme modified cereals contain intact β-glucans, proteins, and natural sugars. The non-dairy cereal dispersions are prepared by the process comprising the steps of:

(i) providing a cereal suspension;
(ii) providing a starch degrading enzyme composition devoid of β-glucanase and proteinase activity and that includes α-amylase and β-amylase, and (iii) treating the cereal suspension with the enzyme composition by introducing the β-amylase and the α-amylase simultaneously to the cereal suspension to provide for:
(a) accelerated enzymatic hydrolysis, and
(b) reduced amounts of the enzymes as compared to the larger amounts that would be required if the enzymes would be introduced sequentially.

Non-dairy, ready-to-use, milk substitute, cereal dispersions, which contain intact β-glucans, proteins, and natural sugars may also be prepared by:
(i) providing a dehulled and heat treated oat suspension which comprises from about 5 to about 20 percent w/w oats in water,
(ii) providing a starch degrading enzyme composition devoid of β-glucanase and proteinase activity and that contains α-amylase and β-amylase, and
(iii) treating the cereal suspension with the enzyme composition by introducing the β-amylase and the α-amylase simultaneously to the cereal suspension to provide for:
(a) accelerated enzymatic hydrolysis, and
(b) reduced amounts of said enzymes than otherwise needed when the enzymes are introduced sequentially,
whereby the natural flavor and aroma of the oat cereal are retained.

The previously discussed non-dairy, ready-to-use cereal dispersions may be consumed in place of dairy milk products, as well as being used in recipes for cooking and for making other non-dairy or dairy-containing products, such as yogurts, ice creams, and other confectionary products. Such products will be characterized as being thick, creamy, homogenous dispersions all containing intact β-glucans, proteins, and natural sugars, wherein the oat suspension comprises from about 0.1 to about 5.0 FAU (α-amylase activity units as defined below) of α-amylase and from about 1400 to about 1600 DP° units (β-amylase activity units as defined below) of β-amylase wherein only up to 40 percent of the oat starch is converted to maltose.

The previously discussed non-dairy, cereal suspensions also may be utilized to produce creamy, dispersions having low viscosity and containing intact β-glucans, proteins, and natural sugars, wherein the oat suspension comprises from about 5.0 to about 10.0 FAU of said α-amylase and from about 1400 to about 1600 DP° of said β-amylase wherein greater than 40 percent of oat starch is converted to maltose.

In all of the above discussed non-dairy, ready-to-use, milk substitute cereal dispersions the α-amylase and the β-amylase are introduced to the cereal suspension simultaneously to provide for shorter enzyme treatment times and to reduce the amounts of enzymes needed.

The method of making the homogeneous and stable improved cereal dispersions may also include performing at least one finishing process step on the enzyme treated non-dairy cereal dispersions and the products made therefrom, such as ice creams, cooking creams, creamy palatable beverages, and yogurts.

The finishing process steps that may improve the shelf-life of the cereal dispersions, or other ready-to-consume dispersion based products, may include: removing coarse particles by centrifuging or decanting; homogenizing the enzyme treated suspension; and/or subjecting the product to Ultra High Temperature (UHT) treatments disclosed in *Food Engineering and Dairy Technology*, H. G. Kessler, Verlay A. Kessler, 1981, Chapter 6, pp. 139–207, the contents of which are incorporated-by-reference herein. After UHT treatment, the product may be aseptically packaged. Additional processes for improved shelf life may include pasteurization and refrigeration until used; or the end product may be evaporated and subsequently spray dried to yield a stable powder. Preferably, the dispersion prepared from the enzyme treated suspension is homogenized, subjected to UHT, and aseptically packaged.

Enzyme activity may be terminated or removed from the enzyme treated suspension before processing for improved shelf life. As an alternative, the enzyme activity may be terminated during some of the processes that improve the self-life of the product, such as the UHT process.

The non-dairy, milk substitute cereal dispersions described above, and in particular the non-dairy milk substitute, viscous oat milk dispersions also described above, can be used in preparing non-dairy ice creams. Although these ice creams contain intact β-glucans, proteins, and natural sugars, such products can be fortified with additional nutrients and flavorings thereby upgrading the product.

The non-dairy, milk substitute cereal dispersions described above, and in particular the non-dairy milk substitute, non-viscous oat milk dispersions also described above, may be used as nutritious beverages having natural cereal flavors without further additions or processing. However, if preferred, fruit or other flavored ingredients, may be added to enhance flavor and nutritional value.

Other commercially important non-dairy recipes can employ the ready-to-use oat milk dispersion milk substitutes of this invention. Representative examples include, non-dairy, oat-based cream, whipped cream, and buttermilk. A preferred cereal dispersion used to make the cooking creams is the non-dairy, oat milk having a low viscosity.

These and other features, aspects, and advantages of the present invention will become better understood with reference to the following description and appended claims.

DESCRIPTION

Definitions

For purposes of this invention, the terms and expressions below, appearing in the specification and claims, are intended to have the following meanings.

"Heat-treated oat product" as used herein refers to dehulled and heat-treated grains (groat), rolled oats, or oat flour as described in detail below.

"Free enzymes" as used herein refers to enzymes which are free to move in the suspension and are not restricted by containment or affixed to a substrate.

"Immobilized enzymes" as used herein means free enzymes that are physically confined by different methods including, but not limited to, semi-permeable membranes, hollow bore fibers, or ultra-filtration membranes.

"FAU" (fungal amylase unit) is the quantity of α-amylase enzyme that will convert a quantity of cereal starch to maltose or to maltose syrups, under "standardized" conditions. GENENCOR International®, the supplier of α-amylase under the name Myclolase, defines FAU as the quantity of enzyme that will convert 1 g of soluble starch per hour in a product having an equal absorption to a reference color at 620 nm after reaction with iodine, where the pH=5.0, T=30° C., reaction time=15–25 min.

"DP°/ml" as used herein is defined as the unit of activity of β-amylase. GENENCOR International®, a supplier of β-amylase under the name SPEZYME BBA 1500, defines DP°/ml as the Degree of Diastatic Power which is the amount of enzyme contained in 0.1 ml of a 5 percent solution of the sample enzyme preparation that will produce sufficient reducing sugars to reduce 5 ml of Fehling's solution, when the sample is incubated with 100 ml of substrate for 1 hour at 20° C.

"Preprocessed cereal suspension" as used herein means a product that has been previously processed by the method disclosed in U. S. Pat. No. 5,686,123.

"Cereal substrate" as used herein means a suspension selected from the group consisting of cereal meal suspensions, preprocessed cereal suspensions, and mixtures thereof.

"Oatmeal suspension" as used herein refers to suspensions comprising oat flour and/or rolled oats.

Concise Statement

According to the invention, there is provided an enzyme preparation for the enzymatic hydrolysis of constituents in a cereal substrate suspension, comprising at least one hydrolase enzyme having the ability to hydrolyze α-glycosidic bonds. The hydrolases may be selected from the group consisting of β-amylase, α-amylase, amyloglucosidase, pullulanase, and mixtures thereof. Preferably, when the enzyme preparation comprises β-amylase or α-amylase there is a mixture of at least one other of the named α-glycosidic hydrolases, and more preferably, when there are two or more enzymes combined in the enzyme preparation, the enzymes are introduced simultaneously to the cereal substrate suspension.

In preferred embodiments of the invention, the enzyme preparations may comprise pullulanase solely; amyloglucosidase solely; or several different combinations of hydrolases including: a mixture combining β-amylase with pullulanase; a mixture combining β-amylase, pullulanase and amyloglucosidase; a mixture combining β-amylase and α-amylase; and a mixture combining α-amylase, β-amylase and amyloglucosidase. Any of the above enzyme preparations comprising a hydrolase alone, or in combination with another, may further comprise an isomerase, such as glucose isomerase.

Any of the above enzyme preparations comprising a hydrolase alone or in combination with another may further comprise an isomerase, such as glucose isomerase.

According to a preferred embodiment of this invention, there is provided an enzyme preparation, comprising α-amylase and β-amylase, for the enzymatic hydrolysis of constituents in a cereal substrate suspension. These enzymes have the ability to hydrolyze α-glycosidic bonds. It is understood that the α-amylase and β-amylase enzymes are introduced simultaneously to the cereal suspension.

Cereal Grains

Generally, the grain that is incorporated into the cereal meal suspension may be any starting grain material including, but not limited to, oats, barley, rice, wheat, maize, rye, sorghum, triticale, and pearl millet. Preferably, the grain is oats. As stated above, oats have properties that make them especially desirable from a consumer point of view because of the large amounts of high molecular weight β-glucan, which are natural hydrocolloids. In suspensions produced by enzymatic hydrolysis with the enzyme preparations of the present invention, the β-glucans found in oats function as indigenous stabilizers. Therefore, the cereal suspensions of the present invention may be used in food for thickening, gelling, or for their emulsion stabilizing effects.

Cereal suspensions according to the invention can be used in the same fields as the products disclosed in U.S. Pat. No. 5,686,123, that is as a milk substitute and as the basis of, or as an additive in, the manufacture of ice-cream, gruel, yogurt, milkshakes, and snacks.

All cereal products, regardless of their end state, are subjected to the same initial treatment. Oats, as well as the other cereals, are first dehulled. The dehulled grains are then treated with steam to inactivate enzymes inherent in oats, such as lipase and peroxidase. These enzymes have a detrimental effect on the taste of the final oat product because they promote lipid oxidation. Oats, especially, are rich in lipids, especially unsaturated lipids that are oxidation-sensitive. Dehulled and heat-treated oat grains (groat) may then be used as the starting material for an end product, or the groat may be treated further to produce either rolled oats or oat flour. When the groat is subjected to a second heat treatment and then pressed, rolled oats (flakes) will be produced. Oat flour is produced when the groat is subject to a second heat treatment that is followed by milling in place of pressing. Wet milling may initiate the preparation of the oat milk as it makes the starch accessible to the enzyme(s). It is an advantage if the meal is finely ground such that it can pass through a bolter with a mesh of 0.8–1 mm.

Any of these oat products may be used to produce the non-dairy, cereal dispersions and ready-to-use oat milks of this invention. For convenience, the use of oats, in their rolled oat form, is preferred because they are readily available, packed in sacks, and are storage stable, however, the use of groat is more economical.

If the oat meal is produced by dry grinding, the dry oat meal is then mixed with water to form a solids/liquid suspension. The water is kept agitated while adding the oats and maintained at a temperature of 50–53° C. Suitably, the slurry or suspension has a weight ratio of meal to water in the range of about 1:6 to about 1:9, which corresponds to a dry solids content of about 10 to about 15% w/w. The suspension is kept agitated until the meal has been completely dispersed. The slurry should have a pH of at least 5 to about 8. This pH range has been found to be effective when adding the enzyme preparations of the present invention. Within this pH range the enzyme preparations have acceptable catalytic activity and the use of additives to alter the pH can be avoided.

In order to remove the coarse particles, the suspension may then be centrifuged or decanted at 350–450 G for about 10–15 minutes.

The aqueous oat suspension is then treated with a starch degrading enzyme composition that is devoid of beta-glucanase and proteinase activity. Enzyme modification yields the desired physicochemical and organoleptic characteristics to the oat milk. The relative amounts of enzymes, such as α-amylase and beta-amylase, added will depend on the desired viscosity of the end product, and is discussed below.

Enzyme Preparations

The enzyme preparations of the present invention convert cereal starch, which comprises both amylose and amylopectin, to high molecular weight maltodextrins and low-molecular-weight compounds of various degrees of modification, such as maltotriose, maltose, and glucose. For instance, β-amylase hydrolyzes α-1–4 glycosidic bonds sequentially from the non-reducing terminal end of amylose and amylopectin with a cleaved product of maltose; α-amylase hydrolyzes internal α-1–4 glycosidic bonds on both amylose and amylopectin with a cleaved maltodextrin; and amyloglucosidase hydrolyzes α-1–4 and 1–6 glycosidic bonds on the non-reducing end of the starch releasing glucose molecules. Therefore, a combination of hydrolases having the ability to hydrolyze α-glycosidic bonds will provide various ratios of maltodextrin/sugar in an enzyme treated cereal suspension.

The choice of enzymes and the reaction time determine the degree of degradation and product spectra. Different species of di- and monosaccharides are produced by using different enzyme preparations which include the combination of at least one α-glycosidic hydrolase and/or an isomerase. The end products could include the disaccharide, maltose, and the monosaccharides, fructose, and glucose. For example, the debranching enzyme pullulanase together with β-amylase will accumulate large amounts of maltose. Amyloglucosidase and glucose isomerase may result in the production of fructose and glucose.

A cereal starch may be converted entirely to low molecular weight compounds, such as glucose by combining, for example, β-amylase, α-amylase, and amyloglucosidase. Glucose isomerase, solely, will result in the production of fructose when added to a cereal substrate that already contains glucose. In the alternative, the enzyme preparation wherein β-amylase, α-amylase, and amyloglucosidase are combined with glucose isomerase may also produce a product with high levels of fructose.

When α-amylase and β-amylase are simultaneously added to the cereal suspension, the α-amylase acts as a catalyst, promoting both the rate of reaction of the β-amylase and the yield. This synergy produces an oat milk rich in maltose and enables maltose and maltodextrin units to be produced while using a smaller amount of enzymes, and in less time, than if the enzymes are used separately. Increasing the concentration of α-amylase to β-amylase yields increasing amounts of maltose.

The enzyme preparations, being a single enzyme or a mixture of enzymes, may treat a cereal substrate suspension of the present invention by introducing free enzymes directly into a cereal substrate suspension, or in the alternative, introducing the cereal substrate suspension to a vessel containing immobilized enzymes.

Usually, free enzymes or cells are not re-used because they are too small to filter and recovery may become cost prohibitive. Hence, elimination of the bio-catalytic activity of free enzymes in the present invention is usually accomplished by denaturing of the enzyme.

The use of immobilized enzymes, whether soluble or insoluble, is effective in that many enzymes can be simultaneous immobilized, by selectively controlling substrates and products through membrane selectivity. As used in the present invention immobilized enzymes provide for ease of loading and treating the cereal meal suspension in a continuous mode reactor. The benefits of immobilized enzymes include complete recovery of the enzymes from the reaction mixture whether used in a batch or continuous mode operation. Thus, the enzymes can be used repeatedly without any contamination of the final product and without the need to heat the product so as to denature the enzyme. Also, larger concentrations of immobilized enzyme can be utilized because the immobilized enzymes can be recovered and re-used, resulting in a shortening of reaction time and/or the size of the vessel needed to carry out the reaction. Another advantage is the virtual absence of enzyme in the final product, so that the enzyme only has to be approved as a food processing aid and not as a food additive even when heating and subsequent enzyme inactivation is not included in the process.

It is further contemplated by the inventors that the enzymes used to prepare the enzyme modified suspensions and/or the homogeneous and stable improved cereal suspension may include enzymes derived from whole cells, organelles, or even microorganisms used as biological catalysts in a fermentation process.

In the present invention the overall conditions including temperature, pH, and the addition of other substrates, such as enzyme cofactors or buffering agents will determine the enzyme activity, and therefore, the yield and quality of the end product. It is known that enzymes extracted from different sources may catalyze the same reaction. For instance, α-amylase from the fungal organism *Aspergillus oryzae* has a optimum pH of 4.7 and an optimum temperature of 50° C., while α-amylase from the bacterium *Bacillus lichenformis* has a pH optimum of 7.5 and an optimum temperature of 90° C. Thus understood, operating conditions, including the amount of enzyme, the temperature of the slurry, the agitation time, and the pH value, are optimized to obtain a final product of suitable viscosity. Techniques used for determining optimal parameters are well known and widely used in the art.

The cereal substrate suspensions of the present invention are treated with the enzyme preparations under carefully regulated operating temperatures. The temperature is chosen to favor enzymatic performance allowing both fast hydrolytic rates and good enzyme stability. A temperature from about 40° C. to a temperature below that which would denature the enzyme, or a combination of enzymes, is generally employed, preferably from about 50 to about 90° C. depending on the enzyme. At lower temperatures the enzyme activity may be low and at higher temperatures the enzyme stability may be low. Accordingly, the temperature of the catalytic reaction is chosen to optimize production of the end products while maintaining the stability of the enzyme preparation. The present invention is also applicable to thermostable starch degrading enzymes, in which case the operating conditions can be adapted to the characteristics of such enzymes.

A hydrolase and/or combination of several hydrolases are introduced to a cereal substrate suspension in a sufficient amount to hydrolyze α-glycosidic bonds of constituents in the cereal substrate suspension to provide an end product with the desired viscosity. The combination of enzymes and amount of each specific enzyme results in suspensions that contain different sugars and varying amounts of each sugar. High concentrations of low molecular weight sugars, such as maltose and glucose, in the end product yield low viscosity cereal dispersions. In contrast, high concentrations of high molecular weight maltodextrin yield viscous products that may be used in soups or yogurts because of their thicker consistency.

Accordingly, varying the kind and/or the amount of enzymes in the mixture will yield specially designed products. Using specific combinations of enzymes helps to standardize the process, so that end products are related to the enzyme combinations, as compared to varying the reaction times, or other process parameters, which does not greatly affect the end product.

In carrying out the present invention, it is generally advantageous to employ between about 1 to about 100 ml of enzyme preparation per kilogram of oats or other grain material that makes up the cereal substrate suspension. The suspension may be treated with an enzyme preparation chosen to produce a final product having the viscosity of about water or of about 10 mPas to about several hundreds of mPas at a sheer rate of about 500 to about 1000 $s^{-1}$. A representative enzyme is α-amylase, which converts cereal starch to maltose or to maltose syrups. The activity of α-amylase is given in FAU (fungal amylase unit). FAU is defined by GENENCOR International®, the supplier of α-amylase under the name Myclolase, as discussed in the definition section, above. NovoNordisk, who supplies an α-amylase under the name Fungamyl®, defines an FAU as the amount of enzyme that breaks down 5.26 g soluble starch (Merck, Amylum soluble Erg. B.6, Batch 9947275) per hour at pH=4.7, reaction time=7–20 min.

The sweetness of the cereal milk, resulting from modifying an oat suspension with enzymes, can be regulated and/or manipulated using appropriate enzyme preparations. In fact, the enzyme preparations of the present invention may be introduced in several steps to tailor-make the end product. For instance, an enzyme preparation comprising α- and ,β-amylase may produce a high level of maltose. With a second treatment of an enzyme preparation comprising amyloglucosidase and/or glucose isomerase, the maltose can be converted to glucose and fructose. The production of glucose, and particularly, of fructose will result in a sweeter suspension than one containing mainly maltose. A suspension comprising fructose has the significant advantage in that fructose presents no adverse affects to diabetics.

The specific type of sugar affects not only the properties of the suspension but also the organoleptic properties of products produced using the suspensions. By altering the sugar profile, it is possible to tailor the functional properties of suspensions, such as viscosity; nutritional properties, and sugar ratio content to meet the needs of the final product.

Enzymatic activity may be discontinued or terminated in the enzyme modified cereal suspension, or in the enzyme treated cereal suspension, by any method well known in the art, including denaturation, centrifugation, chromatographic techniques, and/or separation of the suspension from the immobilized enzymes. Preferably, the enzyme reaction is terminated by heating the cereal suspension to at least 80° C., and more preferably, between about 80 to 90° C. At low water contents a higher temperature is needed for the inactivation of the spoiling enzymes than that at higher water contents. At high moisture levels a lower temperature is sufficient to achieve an equal degree of enzyme inactivation. As an alternative, enzyme activity may be discontinued/terminated during the final process steps that improve the shelf life of the product.

Using the cereal suspensions of the present invention, homogeneous and stable improved cereal dispersions having the aroma and taste of natural cereals and containing intact β-glucans, proteins, and natural sugar are prepared by treating the suspensions with enzyme preparations provided by the present invention.

Finishing Treatments

Representative final process steps may include: removing coarse particles by centrifuging or decanting; homogenizing the enzyme treated suspension at a temperature of about 42 to about 45° C., at a pressure of about 200 to about 250 bar; or subjecting the product to Ultra High Temperature (UHT) treatments disclosed in Food Engineering and Dairy Technology, H. G. Kessler, Verlay A. Kessler, 1981, Chapter 6, pp. 139–207, the contents of which are incorporated by reference herein. After UHT treatment, the product may be aseptically packaged. Centrifugation, removes insolubles that otherwise yield grittiness. Homogenization promotes smooth mouth feel and prevents sedimentation with long term storage. Additional processes for improved shelf life may include pasteurization to kill spoilage microorganisms thereby prolonging shelf life, refrigeration until used; or the end product may be evaporated and subsequently spray dried to yield a microbiologically stable powder and facilitate handling and transport.

Preferred Embodiments

In one embodiment, the cereal substrate suspension is a cereal meal suspension. The cereal meal suspension is prepared by dry or wet grinding rolled cereals, or otherwise heating and water treating cereals to meal, and suspending the cereal meal in water to form a cereal meal suspension. Optionally, the suspension may be centrifuged or decanted in order to remove coarse fiber particles before being treated with the enzyme preparation.

Conveniently, the cereal meal suspension is prepared on the basis of commercially produced, pre-gelatinized rolled oats retaining the original taste and aroma of the oats. The rolled oats are ground to oatmeal by total, dry or wet grinding. In dry grinding, the oatmeal is suspended in water, preferably at a temperature of 50–65° C. Also in wet grinding, water is used preferably at a temperature of 50–65° C. Especially good results are obtained if the water has been deionized.

For a majority of starches, contained within the cereal meal, the heating of the suspension to a temperature between 50 to 65° C. gelatinizes the cereal starch for easier hydrolyzation. However, some oats contain resistant starches that are not gelatinized at these temperatures, and therefore, are not easily hydrolyzed by the enzyme preparations of the present invention. In this instance, it has been found to be beneficial to initially hydrolyze the non-resistant starch in a first enzyme treating step with the enzyme preparations of the present invention and then subjecting the suspension to higher temperatures, preferably above 100° C. to gelatinize the resistant starch. The suspension is subsequently cooled to a workable temperature and standard conditions. The suspension is the retreated with the enzyme preparations of the present invention. This method will allow for more complete hydrolyzation of substantially all the cereal starch including the resistant starch in the cereal meal suspension.

In a further embodiment of the present invention, a preprocessed cereal suspension may be used. The cereal meal suspension is treated with β-amylase in a first enzyme treatment step that specifically generates maltose units and has no glucanase and proteinase activity, to a viscosity of 3–0.1 Pas at the shear rate of 10–100 s$^{-1}$. Then the suspension is treated with α-amylase in a second enzyme treatment step that specifically generates maltose units and has no glucanase and proteinase activity, to a viscosity of less than 0.5 Pas at the shear rate of 10–100 s$^{-1}$. This preprocessed cereal suspension may then be further treated by the enzyme preparations of the present invention. Optionally, the preprocessed cereal suspension may be homogenized and/or subjected to UHT treatment.

The invention will now be described in more detail by the following non-limiting examples.

EXAMPLE 1

Pre-gelatinized rolled oats were wet-milled at a temperature of about 52 to about 63° C. were used to prepare a suspension where the concentration of the milled oats in water was about 10 to about 15% w/w. An enzyme preparation according to the invention which comprised barley β-amylase (Genencor Intl., Rochester, N.Y., USA; or Rhodia Ltd, Cheshire, UK) and pullulanase, a debranching enzyme, e.g. Promozyme (Novo Nordisk, Bagsvaerd, Denmark), was added to the cereal meal suspension at a concentration of approximately 2 ml per kg of oats and at a temperature of about 58 to about 61° C. The concentration of the enzymes in the enzyme preparation was about 500 to about 1000 DP° and about 150 to about 300 PU (pullulanase units) per ml, respectively. The enzyme preparation was allowed to act for 1–2 hours, or until the viscosity of the suspension dropped to between about 20 to about 40 mPas at a shear rate of around 700 s$^{-1}$. The product contained large amounts of maltose. The majority of starch (approximately 60% of the oats) was converted to maltose. The suspension was then heated to about 85 to about 90° C. to inactivate the enzymes. The product was decanted to remove the excess of non-soluble fiber, and homogenized. Optionally the product could be UHT treated and aseptically packed, pasteurized and kept refrigerated until used, or it is evaporated and subsequently spray dried to yield a stable powder.

EXAMPLE 2

Pre-gelatinized rolled oats were milled as in Example 1. An enzyme preparation according to the invention comprised of barley β-amylase (Genencor Intl., Rochester, N.Y., USA; or Rhodia Ltd, Cheshire, UK), pullulanase, a debranching enzyme, e.g. Promozyme (Novo Nordisk, Bagsvaerd, Denmark) and amyloglucosidase, e.g., AMG (Novo Nordisk, Bagsvaerd, Denmark) or Optidex (Genencor Intl., Rochester, N.Y., USA) was added to the oat meal suspension at a concentration of about 3 to about 4 ml per kg oats and at a temperature of about 58 to about 61° C. The concentration of these enzymes in the enzyme preparation was about 400 to about 700 DP°, about 100 to about 200 PU (pullulanase units), and about 90 to about 110 AGU per ml, respectively. The enzyme preparation was allowed to act for about 1 to about 2 hours, or until the viscosity of the suspension dropped to about 20 to about 40 mPas at a shear rate of 700 s$^{-1}$. The product contained large amounts of glucose. Finally, the suspension was heated and treated as in Example 1.

EXAMPLE 3

Pre-gelatinized rolled oats were milled as in Example 1. An enzyme preparation according to the invention which comprised a mixture of β-amylase (Genencor Intl., Rochester, N.Y., USA; or Rhodia Ltd, Cheshire, UK) and endo-acting α-amylase, e.g. Fungamyl (Novo Nordisk, Bagsvaerd, Denmark) or Mycolase (Genencor Intl., Rochester, N.Y., USA), was added to the cereal meal suspension at a concentration of approximately 2 ml per kg of oats and at a temperature of about 54 to about 57° C. The concentration of these enzymes in the enzyme preparation was about 1400 to about 1600 DP° and about 30 to about 70 FAU (amylase units) per ml, respectively. The enzyme preparation was allowed to act for about 1 hour, or until the viscosity of the suspension dropped to about 20 to about 40 mPas at a shear rate of about 700 s$^{-1}$. Most of the oat starch (60–70%) was converted to maltose and the rest was present as maltodextrins (step 1). Then (in step 2), another exo-acting enzyme was added, e.g. amyloglucosidase AMG (Novo Nordisk, Bagsvaerd, Denmark) or Optidex (Genencor Intl., Rochester, N.Y., USA), at a dosage of approximately 600 AGU (amyloglucosidase units) per kg of oats. The reaction was terminated when the desired amount of glucose had been produced. For example, 30 minutes after the addition of amyloglucosidase (glucoamylase), the suspension contained equal amounts of maltose and glucose while the maltose content was 50% of the suspension in step 1. The maltose content was high in step 1, and amyloglucosidase rapidly hydrolyzed this substrate. As the maltose content decreased, maltodextrin became the preferred substrate and also became increasingly hydrolyzed. At full conversion all the starch was converted to glucose. Finally, the suspension was heated and treated as in Example 1.

EXAMPLE 4

Pre-gelatinized rolled oats were milled as in Example 1. An enzyme preparation according to the invention which comprised a mixture of barley β-amylase (Genencor Intl., Rochester, N.Y., USA; or Rhodia Ltd, Cheshire, UK), α-amylase, e.g. Fungamyl (Novo Nordisk, Bagsvaerd, Denmark) or Mycolase (Genencor Intl., Rochester, N.Y., USA) and amyloglucosidase, e.g., AMG (Novo Nordisk, Bagsvaerd, Denmark) or Optidex (Genencor Intl., Rochester, N.Y., USA) was added to the suspension at a dosage of about 3 to about 4 ml per kg oats and at a temperature of about 54 to about 57° C. The concentration of these enzymes in the enzyme preparation was about 700 to about 900 DP°, about 1 to about 35 FAU (α-amylase units) and about 200 to about 350 AGU per ml, respectively. The enzyme preparation was allowed to act for about 1–2 hours, or until the viscosity of the suspension dropped to about 20 to about 40 mPas at a shear rate of about 700 s$^{-1}$. Finally, the suspension was heated and treated as in Example 1.

EXAMPLE 5

A suspension of oats was prepared as in U.S. Pat. No. 5,686,123 is treated with an enzyme preparation according to the invention and which comprised barley β-amylase (Genencor Intl., Rochester, N.Y., USA; or Rhodia Ltd, Cheshire, UK) and pullulanase, a debranching enzyme, e.g. Promozyme (Novo Nordisk, Bagsvaerd, Denmark), at a concentration of approximately 2 ml per kg of oats. Alternatively, the suspension was treated with a debranching enzyme, such as pullulanase, e.g., Promozyme (Novo Nordisk, Bagsvaerd, Denmark), at a concentration of approximately 800 PU per kg of oats. Otherwise the conditions were the same as in Example 1. The product was high in maltose and contained essentially no maltodextrins.

EXAMPLE 6

A suspension of oats was prepared as in U.S. Pat. No. 5,686,123 and was treated with the same enzyme preparation as in Example 2, or with amyloglucosidase as in Example 3 (as in step 2). The product contained a decreasing amount of maltodextrins and an increasing amount of glucose as the hydrolytic reaction proceeded.

EXAMPLE 7

To any of the products of Examples 2, 3, 4 and 6, i.e., which contained glucose, there was added an enzyme preparation according to the invention which comprised amyloglucosidase of about 50 to about 60 AGU per ml, e.g., AMG (Novo Nordisk, Bagsvaerd, Denmark) or Optidex (Genencor Intl., Rochester, N.Y., USA) and glucose isomerase (about 3000 GIU per ml), at a concentration of about 18 to about 70 ml per kg of oats, or only glucose isomerase, e.g. Spezyme GI (Genencor Intl., Rochester, N.Y., USA) or Sweetzyme (Novo Nordisk, Bagsvaerd, Denmark), at a concentration of about 50,000-to about 200,000 GIU (glucose isomerase units). Within two (2) hours, 25% of the glucose was converted to fructose.

EXAMPLE 8

A ready-to-use, non-dairy, thick oat milk was prepared by the following method. About 10 to about 15 percent w/w of oat cereal meal was suspended in water that was heated to 50–65° C. The meal can be dry or wet ground, rolled oats, or otherwise heat and water treated cereal. For convenience, the cereal meal suspension was prepared using commercially produced, pre-gelatinized rolled oats. The suspension was maintained at a temperature of 50 to 65° C. to gelatinize the cereal starch for easier hydrolyzation of most of the starch in the cereal meal. An enzyme preparation of the present invention comprising a mixture of β-amylase (Genencor Intl., Rochester, N.Y., USA; or Rhodia Ltd, Cheshire, UK), and endo-acting α-amylase, e.g. Fungamyl (Novo Nordisk, Bagsvaerd, Denmark) or Mycolase (Genencor Intl., Rochester, N.Y., USA) was then added to the aqueous oat suspension at a concentration of about 1 to about 3 ml of enzyme(s) per kg of oats at a temperature of about 54 to about 64° C. The α-amylase and β-amylase were added simultaneously while the suspension was kept under continuous agitation. An incubation temperature was maintained at 53–55° C.

The simultaneous addition of the β-amylase with the α-amylase provided accelerated enzymatic hydrolysis, and the use of lesser amounts of said enzymes than otherwise needed, when the enzymes were added separately. The concentration of these enzymes in the enzyme preparation was about 1400 to about 1600 DP° and about 0.5 to about 2 FAU per ml, respectively. The enzyme preparation was allowed to act on the oat cereal for approximately 2 hours, or alternatively, until the viscosity of the milk was measured at 60,000 cP at a concentration of 10 percent and at 4° C. measured with a Brookfield viscometer at 0.3 rpm. About 40 percent of the starch was converted. Therefore, due to the high content of the high molecular weight maltodextrin, this product was quite thick.

It is optional, at this point, to homogenize the enzyme-treated milk product at a pressure of 200 bar (homogenization should be carried out in the range of 160–250 bar) and at a temperature of 72–75° C. The non-dairy oat milk may then be subjected to indirect vapor at a temperature of 137–138° C. for 3–4 seconds in order to sterilize the dispersion. This sterilization process kills bacteria and spore-forming agents, and inactivates the added enzymes before the product is packed aseptically.

The resulting high viscosity oat milk was homogeneous and stable, contained intact β-glucans and proteins, retained the taste and aroma of natural oats, had excellent freeze/thaw, water-holding, thickening, and organoleptic (fatty mouth feel) properties, and could be used as prepared, or as a base for other non-dairy oat milk dispersion products. The combination of properties exhibited by this oat product makes it ideal for use as is, or for example, as a frozen desert or an ice cream.

EXAMPLE 9

A ready to use non-dairy oat milk dispersion whole milk substitute having a low viscosity was prepared according to the method of Example 8, except that while the concentration of the β-amylase in the enzyme preparation remained at about 1400 to about 1600 DP°, the concentration of the α-amylase was about 6 to about 8 FAU per ml to yield a low production of maltodextrin relative to the production of maltose resulting in a product with a low viscosity. This creamy oat milk dispersion can be used as is to provide a tasty and nutritious non-dairy beverage or as a base to make creams, beverages, and ice creams.

EXAMPLE 10

As an example of how the high viscosity, non-dairy, oat milk dispersion can be used as a frozen product, a natural fruit flavored ice cream was prepared. A 10% w/w dispersion of oats in water was prepared according to Example 8. Then separately, to 8 percent w/w of a melted vegetable fat, such as Akomix (from Karishamns AB, Karshamn, Sweden) 0.4% w/w of an emulsifier, such as distilled monoglycerides (from Danisco Cultor, Norrkoeping, Sweden), was added. The fat/emulsifier mixture was heated to above 70° C. to solubilize the emulsifier. When the emulsifier was solubilized, 7% w/w sucrose and 8% w/w glucose was added to the emulsified fat. The emulsified melted fat/sugar mixture was then added to the oat suspension. This mixture was then pasteurized at 80° C. for 25 seconds.

Optionally, the mixture may be homogenized at 200 bar prior to cooling overnight.

A flavoring such as vanilla, or a fruit, such as blueberry, or pineapple purée can be added to the cooled mixture. After partially freezing the mixture, air is incorporated into the mixture to yield an overrun value of around 80%, where overrun is the ratio of the volume of ice cream over the volume of unfrozen mix. Prior to consumption, the ice cream is hardened at temperatures below −20° C.

This ice cream, made using the high viscosity oat milk dispersion of Example 8, is able to maintain injected air bubbles, which gives a frozen product, such as ice cream a creamy taste/feel. Because this product also possess an unexpected freeze-thaw stability, there is no need for a stabilizer or added protein.

EXAMPLE 11

A thick, nutritious, tasty fruit/oat milk beverage was prepared using the low viscosity non-dairy oat milk dispersion according to Example 9 by adding to this oat milk dispersion 10 percent w/w desired fruit concentrate. This mixture was then pasteurized at 90° C. for 13 seconds and then homogenized at 200 bar while maintaining the 90° C. temperature. The mixture was then poured into individual storage containers, such as a glass bottle. Alternatively, the product can be cooled to about 4–6° C. and then poured into containers in an aseptic manner. No extra sweetener, acid, stabilizer or flavor are needed to obtain a nutritious and palatable beverage.

EXAMPLE 12

A non-dairy oat ice cream made using the low viscosity oat milk of Example 9 was prepared by melting 8 percent w/w of a vegetable fat, such as Akonix (from Karishamns AB, Karshamn, Sweden) to which 0.4 percent w/w of an emulsifier, such as distilled monoglycerides (from Danisco Cultor, Morrkoeping, Sweden) was added. This fat/emulsifier mixture was then heated to solubilized the emulsifier before the addition of 5 percent w/w sucrose, 5 percent w/w glucose syrup, and 5 percent w/w glucose. To the 10 percent w/w oat milk suspension, 8 percent by weight of the fat/sugar mixture was added. The final mixture was then pasteurized at 80° C. for 25 seconds.

Optionally, at this point, the mixture could be homogenized at 200 bar prior to cooling and either a flavoring and/or fruit added.

The mixture was then partially frozen, air incorporated into the semi-frozen mixture, and finally hardened at temperatures below −20° C.

EXAMPLE 13

A non-dairy, oat-based cream comprising the oat milk of Example 9 was prepared by melting at 70° C. an oil mixture of 50 percent w/w canola oil and 50 percent w/w palm oil. Added to the melted oil mixture was 0.4 percent w/w of an emulsifier, such as distilled monoglycerides. In a separate step, 0.05 percent w/w salt was added to the non-viscous oat milk dispersion. The emulsified fat and salted oat milk were then homogenized at 200 bar with a two-stage homogenizer. The product can then be packaged aseptically, preferably in, 3 dl packages.

This non-dairy, beta-glucan dispersion is ready to be used in any recipe calling for cream.

What is claimed is:

1. A non-dairy, ready-to-use milk substitute comprising beta-glucans, proteins, and sugars prepared by the steps which comprise:

(i) providing an oat cereal suspension;

(ii) providing a starch degrading enzyme composition devoid of β-glucanase and proteinase activity and comprising α-amylase and β-amylase, and (iii) treating said cereal suspension with said enzyme composition by introducing the β-amylase and the α-amylase simultaneously to said cereal suspension to provide for cereal suspensions of differing viscosities with various ratios of low molecular weight sugars and high molecular weight maltodextrins, wherein the concentration of said low molecular weight sugars is higher relative to the concentration of said high molecular weight maltodextrins, and the low molecular weight sugar content of said suspension is higher than would otherwise be achieved with the sequential addition of the same enzymes over the same reaction period.

2. The non-dairy, ready-to-use milk substitute of claim 1 wherein the oat suspension comprises from about 5 to about 20 percent w/w oats in water.

3. The non-dairy, ready-to-use milk substitute of claim 1 further comprising the step of providing a dehulled and heat treated cereal suspension.

4. The non-dairy, ready-to-use oat milk of claim 1 wherein the oat suspension comprises from about 0.1 to about 5.0 FA units of said α amylase and from about 1400 to about 1600 DP° units of said β amylase wherein up to 40 percent of oat starch is converted to maltose.

5. The non-dairy, ready-to-use oat milk of claim 1 wherein the oat suspension comprises from about 5.0 to about 10.0 FA units of said α amylase and from about 1400 to about 1600 DP° units of said β amylase.

6. An ice cream comprising the non-dairy oat milk of claim 4.

7. An ice cream comprising the non-dairy oat milk of claim 5.

8. A non-dairy, fruity, oat beverage comprising the non-dairy oat milk of claim 5.

9. A non-dairy, oat-based ice cream comprising the oat milk of claim 5, said ice cream prepared by the steps comprising:

a) melting from about 1 to about 15 percent w/w vegetable fat, b) adding from about 0.1 to about 10 percent w/w of an emulsifier to said melted fat, c) heating said fat/emulsifier mixture to from about 60 to about 80° C. to solubilize the emulsifier, d) adding from about 1–10 percent w/w sucrose, from about 1–10 percent w/w glucose syrup, and from about 1–10 percent w/w glucose to said emulsified fat to form a fat/sugar mixture;

e) adding from about 1–15 percent w/w of the fat/sugar mixture of step (d) to the oat milk to form a fat/oat/sugar mixture, f) pasteurizing said mixture at a temperature of from about 70 to about 90° C; and d) freezing said pasteurized mixture.

10. The non-dairy, oat-based ice cream of claim 9 including the addition of a flavorant.

11. The non-dairy, oat-based ice cream of claim 9 including the addition of fruit.

12. The non-dairy, oat-based ice cream of claim 9.

13. The non-dairy, oat-based ice cream of claim 9.

14. A non-dairy, oat-based cream comprising the oat milk of claim 5.

* * * * *